(12) United States Patent
Harazin et al.

(10) Patent No.: US 8,115,599 B2
(45) Date of Patent: Feb. 14, 2012

(54) METHODS AND SYSTEMS FOR LOCATING AND IDENTIFYING LABWARE RADIO-FREQUENCY IDENTIFICATION TAGS

(75) Inventors: Richard R Harazin, Lombard, IL (US); Ronald A Zweifel, Naperville, IL (US)

(73) Assignee: PerkinElmer LAS, Inc., Waltham, MA (US)

( * ) Notice: Subject to any disclaimer, the term of this patent is extended or adjusted under 35 U.S.C. 154(b) by 143 days.

(21) Appl. No.: 12/166,477

(22) Filed: Jul. 2, 2008

(65) Prior Publication Data

US 2009/0015430 A1   Jan. 15, 2009

Related U.S. Application Data

(63) Continuation of application No. 11/452,889, filed on Jun. 14, 2006, now Pat. No. 7,411,508.

(60) Provisional application No. 60/595,247, filed on Jun. 17, 2005.

(51) Int. Cl.
*G08B 13/14* (2006.01)

(52) U.S. Cl. ............... 340/10.1; 340/572.7; 340/572.8; 340/572.1

(58) Field of Classification Search .............. 340/10.1, 340/572.7, 572.8
See application file for complete search history.

(56) References Cited

U.S. PATENT DOCUMENTS

| | | | |
|---|---|---|---|
| 5,532,522 A * | 7/1996 | Dietz et al. | 340/5.61 |
| 5,663,545 A * | 9/1997 | Marquiss | 235/375 |
| 5,936,527 A | 8/1999 | Isaacman et al. | |
| 6,005,482 A | 12/1999 | Moran et al. | |
| 6,232,585 B1 | 5/2001 | Clothier et al. | |
| 6,456,239 B1 | 9/2002 | Werb et al. | |
| 6,576,700 B2 | 6/2003 | Patel | |
| 6,812,838 B1 | 11/2004 | Maloney | |
| 6,827,256 B2 * | 12/2004 | Stobbe | 235/375 |
| 6,875,387 B2 | 4/2005 | Mhetar et al. | |

(Continued)

FOREIGN PATENT DOCUMENTS

EP   1 116 774 A2   7/2001

(Continued)

OTHER PUBLICATIONS

Supplemental European Search Report for European Patent Application No. EP 07 110310 mailed Jan. 25, 2008, 8 pgs.

(Continued)

*Primary Examiner* — Jennifer Mehmood
*Assistant Examiner* — Naomi Small
(74) *Attorney, Agent, or Firm* — Lando & Anastasi LLP

(57) ABSTRACT

Methods and systems for automatically locating and identifying labware using radio-frequency identification (RFID) tags are described herein. The methods and systems include a plurality of RFID tags (pre-programmed with unique data codes) that are associated with labware (or labware holders). For example, the RFID tags can be embedded within the locating pegs of the labware (or labware holders). The methods and systems also include a plurality of RFID tag readers that mount near known locations of an instrument deck which receives the labware. The RFID tag readers automatically scan for the presence of RFID tags such that when a piece of labware is added to the instrument deck, and then report to a processing device the specific known location on deck where each tag was found, as well as the unique data code of each tag. Using this information, the methods and systems determine one or more of the location, orientation, and identity of the received labware.

24 Claims, 2 Drawing Sheets

U.S. PATENT DOCUMENTS

| | | |
|---|---|---|
| 6,998,983 B2 | 2/2006 | Charych et al. |
| 7,019,650 B2 | 3/2006 | Volpi et al. |
| 7,198,193 B2 | 4/2007 | Hassan-Zade et al. |
| 7,411,508 B2 | 8/2008 | Harazin et al. |
| 2001/0028308 A1 | 10/2001 | De La Huerga |
| 2002/0067270 A1 | 6/2002 | Yarin et al. |
| 2003/0018131 A1 | 1/2003 | Davis et al. |
| 2003/0213845 A1* | 11/2003 | Hermann et al. ............. 235/385 |
| 2004/0088075 A1 | 5/2004 | Batcher |
| 2005/0205673 A1* | 9/2005 | Morris et al. ................. 235/385 |
| 2006/0018996 A1 | 1/2006 | Pollock et al. |
| 2006/0059964 A1 | 3/2006 | Bass et al. |
| 2006/0085162 A1 | 4/2006 | Bjornson et al. |
| 2006/0101129 A1 | 5/2006 | Rubertelli et al. |
| 2006/0119481 A1* | 6/2006 | Tethrake et al. ........... 340/572.1 |
| 2006/0244593 A1 | 11/2006 | Nycz et al. |
| 2008/0042839 A1* | 2/2008 | Grater et al. .............. 340/572.1 |

FOREIGN PATENT DOCUMENTS

| | | |
|---|---|---|
| EP | 1726362 A1 | 11/2006 |
| WO | 96/37532 A1 | 11/1996 |
| WO | 2005098455 A1 | 10/2005 |
| WO | 2006000620 B1 | 1/2006 |
| WO | 2007024540 A1 | 3/2007 |

OTHER PUBLICATIONS

"IVF WitnessTM: Eliminate Human Error in IVF", http://www.research-instruments.com/ie/ivf/witness.htm, retrieved on May 22, 2006, pp. 1-4.

International Search Report for PCT/US2006/43843 mailed Oct. 29, 2007.

Extended Supplementary European Search Report for PCT/US2006/43843 dated Dec. 3, 2009.

\* cited by examiner

METHODS AND SYSTEMS FOR LOCATING AND IDENTIFYING LABWARE RADIO-FREQUENCY IDENTIFICATION TAGS

PRIORITY CLAIM

This application is a continuation application of, and claims the priority benefit of, U.S. application Ser. No. 11/452,889 filed on Jun. 14, 2006. U.S. application Ser. No. 11/452,889 claims priority to U.S. Provisional Application No. 60/595,247 filed on Jun. 17, 2005, the entire disclosure of which is hereby incorporated herein by reference in its entirety.

BACKGROUND

1. Technical Field

The present disclosure relates to the use of radio-frequency identification (RFID) techniques for locating and identifying labware used in biochemical and chemical processing as well as in the analysis of samples in laboratories and the like.

2. Description of Related Art

Automated liquid handling and chemical analysis instruments have been developed for biochemical and chemical processing and analysis of samples. These instruments generally use different types of labware to process the samples. These labware items can be containers in which samples are held (e.g., test tubes, micro-titer plates), holders for the sample containers (e.g., a test tube rack), holders for accessories (e.g., a disposable pipette rack), processing items (e.g., heaters, chillers, washbowls), or various other accessories. Such labware is available from a number of sources including PerkinElmer Life & Analytical Sciences.

Labware placed onto an instrument, workstation, work area, instrument deck, and the like, is typically identified manually. It is also known in the art to identify the labware semi-automatically by applying a bar code identifying label to the labware and using a bar code wand or reader to recover labware identification information.

Another prior art system describes the use of RFID tags that are attached to sample vials so that the vials may be identified when stored or transferred.

Other prior art systems attempt to automate labware identification using optical means.

SUMMARY

An embodiment of the present disclosure includes a labware item having at least one RFID tag associated therewith, and an instrument deck including at least one RFID reader associated therewith, each RFID reader positioned at a known instrument deck location, wherein the at least one RFID tag is communicatively coupled to at least one RFID reader at least when the labware item is positioned on the instrument deck The RFID reader may comprise an RFID reader antenna coupled to an RFID reading circuit, and a processing unit coupled to the RFID reading circuit and operable based on the read RFD tag to determine at least one of location, orientation, and identity of the labware item.

The labware item may include at least one locating peg, where the at least one RFID tag is associated with the at least one locating peg (for example, the RFID tag may be embedded in the locating peg). The instrument deck may include at least one aperture for receiving the at least one locating peg when the labware item is positioned on the instrument deck. In an embodiment, a printed circuit board is mounted underneath the instrument deck and includes an opening, aligned with the aperture in the instrument deck, for receiving the labware item locating peg. The RFID reader antenna can be mounted to the printed circuit board and may be positioned adjacent (for example, surrounding) the opening in the printed circuit board.

Also disclosed is a method, the method comprising associating at least one RFID tag with a labware item, providing a labware instrument deck including at least one RFID reader positioned at at least one known instrument deck location, and reading the REID tag(s) at least when the labware item is positioned on the instrument deck.

The labware item may include at least one locating peg, and associating can comprise associating the at least one RFID tag with the at least one locating peg. Receiving can then comprise receiving the at least one locating peg of the labware item in at least one aperture in the instrument deck when the labware item is positioned on the instrument deck, and reading can comprise reading of the RFID tag associated with the labware item locating peg as received in the aperture.

In an implementation, associating may comprise associating a plurality of RFID tags with the labware item, and reading may then comprise detecting an orientation of the labware item when positioned on the instrument deck based on reading of one or more RFID tags associated with the labware item.

In an implementation, reading may comprise scanning for the presence of RFID tags, and determining, based on the scanned RFID tag, at least one of location, orientation, and identity of the labware item positioned on the instrument deck. Reading may also comprise scanning for the presence of RFID tags at each known instrument deck location, and determining, based on the scanned RFID tag, that a labware item has been added to the instrument deck at the known instrument deck location corresponding to the aperture which received the locating peg of that labware item. Reading may also comprise scanning for the presence of RFID tags at each known instrument deck location, and determining, based on the scanned RFID tag, that a labware item having a unique data code associated with its scanned RFID tag has been added to the instrument deck and is located at the known instrument deck location.

An embodiment of the present disclosure includes a labware item including at least one locating peg and at least one RFID tag positioned within the locating peg(s), an instrument deck including a plurality of apertures, each aperture capable of receiving a labware item locating peg, and a plurality of RFID reader antennas, each antenna being associated with at least one of the plurality of apertures in the instrument deck. A processing unit may be coupled to the RFID reading circuit and operate based on a read RFID) tag within a locating peg of a labware item received by the instrument deck to determine at least one of labware item location on the deck, labware item orientation on the deck, and identity of the labware item.

A printed circuit board may be mounted underneath the instrument deck and include an opening, aligned with the aperture in the instrument deck, for receiving the labware item locating peg. The RFID reader antenna is mounted to (or built into) the printed circuit board and is positioned adjacent (for example, surrounding) the opening in the printed circuit board.

An embodiment of the present disclosure is a labware receiving instrument deck, comprising a labware support deck member for receiving thereon a labware item having an associated RFID tag (or tags), a plurality of RFID reader antennas, each antenna being associated with at least one known location on the support deck member, and circuitry coupled to the plurality of RFID reader antennas for reading the RFID tag(s) associated with a labware item received on the labware support deck member. A processing device coupled to the circuitry further operates to determine at least one of a location, orientation, and identity of the labware item that is positioned on or near the deck member.

The labware support deck member may include a plurality of apertures, each aperture capable of receiving a labware item locating peg within which the RFID tag of the labware item is embedded. The RFID reader antennas can be associated with the apertures in the deck member. A printed circuit board may be mounted underneath the deck and includes an opening, aligned with the aperture in the deck, for receiving the labware item locating peg. The RFID reader antenna may be mounted to (or built into) the printed circuit board and positioned adjacent (for example, surrounding) the opening in the printed circuit board.

An embodiment of the present disclosure is a system comprising one or more RFID tags programmed with unique data codes and embedded within locating pegs of one or more labware items, a plurality of RFID tag readers mounted near locating holes of an instrument deck which receive the locating peg(s) of the labware item(s), and a processing device operable to cause the RFID tag readers to scan for the presence of RFID tags such that when a labware item is positioned on the deck the locating hole(s) receiving the locating peg(s) of that labware item are identified and the unique data code(s) of the embedded RFID tag(s) are read and/or received by the processing device. The processing device can further operate to determine the identity of the labware item that is added to the deck based on the read unique data code(s). The processing device can further operate to determine orientation of the labware item that is added to the deck based on the read unique data code(s) and the identified locating hole(s) receiving the (respective) locating peg(s) of that labware item.

BRIEF DESCRIPTION OF THE DRAWINGS

A more complete understanding of the disclosed methods and apparatus may be acquired by reference to the following Detailed Description when taken in conjunction with the accompanying Drawings wherein.

DETAILED DESCRIPTION OF THE DRAWINGS

Figure 1:
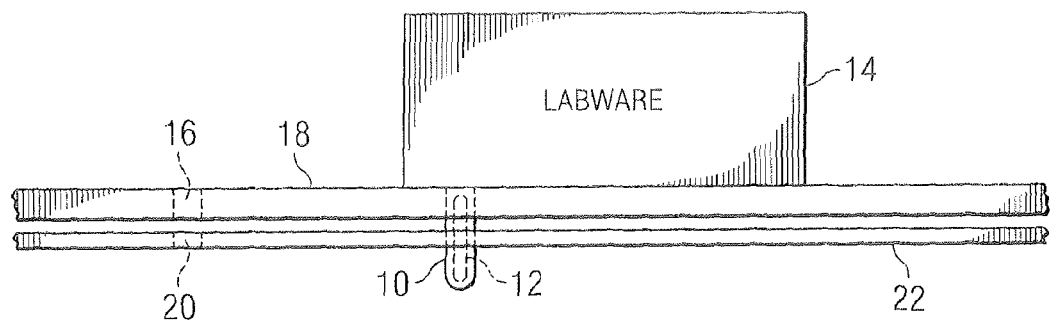
FIG. 1 illustrates one embodiment of the present systems and methods.

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems or methods of the present disclosure.

The present teachings include methods and systems that include passive, low frequency, pre-programmed (with a unique identifying code) radio-frequency identification (RFID) tags to identify, for example, labware presence, location, orientation, and/or type. Because RFID tags are pre-programmed and integrated into and/or otherwise coupled to the labware (e.g., associated with and positioned at a known location on), and RFID readers and/or antenna(e) are coupled to an instrument deck onto which the labware may be placed, labware identification can occur automatically (e.g., without manual intervention) as the labware is positioned on or near the deck (i.e., the labware does not have to be moved to a separate reading device to be identified). Further, in the illustrated embodiments, use of a certain exemplary RFID reader antenna allows the RFID tags to be read (i.e., RFID information is transmitted and received) near a metal instrument deck and/or other situations where RF interference and/or crosstalk might otherwise occur, although it can be understood that other variations of the present teachings may occur. In the illustrated embodiments, for example, the antenna(e) can allow RFID tags to be placed within proximities of about 1.5 inches (about 3.8 centimeters) of each other without interference/crosstalk problems.

Automatic labware identification is useful, for example, in liquid handling and chemical analysis instruments for checking the positions of the labware, tracking the movement of the labware, and/or for ensuring that labware do not collide with each other or that sample handling robotics do not collide with or miss the labware. The labware ID systems and methods presented herein provide an automated way to identify the location, orientation and/or type of labware present on or near the instrument (or more particularly positioned on or near an instrument deck).

In the illustrated embodiments, the pre-programmed RFID tags can be embedded within labware "locating pegs" and hence can be protected from chemical spills, although in other embodiments using locating pegs, the RFID tags may be positioned on the surface of the locating pegs or otherwise associated therewith. It can be understood that use of the term "locating peg" or "location peg" is not intended to limit the size and/or shape of such component, which can vary based on the embodiment, and thus the term "location/locating peg" should be understood to include one or more components that may be adapted for the features substantially similar to those attributed herein to the "location/locating peg". In a more general implementation, the RFID tags may be positioned on the surface of, or within a portion of, the labware at a suitable location as determined by the embodiment.

A multitude of pre-programmed RFID tag readers can be configured in close proximity to each other and associated with the instrument deck. For example, the RFID tag readers may be arranged in an array format with each RFID reader being associated with a known location (or location area) on the instrument deck. In an implementation, the RFID readers can be configured on a printed circuit board, with the circuit board being associated with an instrument deck, thus allowing labware to be identified when positioned on or near the instrument deck. It can further be understood that although the illustrated embodiments employ locating pegs for containment of RFID tags, other embodiments may not include such containment methods but similarly to the illustrated embodiments, may allow for the communications between RFID tags associated with labware (e.g., positioned on/in the labware, etc.) and an antenna(e) of known position relative to the instrument deck, as provided herein.

Reference is now made to FIG. 1 which shows a side view of an embodiment of one locating peg of the labware ID apparatus. In the FIG. 1 embodiment, an RFID tag 12 is embedded into a locating peg 10 of the labware 14, such that when the labware 14 is placed on an instrument deck 18, the tag (and peg) protrudes through an aperture 16 in the instrument deck 18 and further through an aperture 20 in a printed circuit (PC) board 22 (mounted below and spaced away from the deck 18). The PC board includes a plurality of RFID tag reader antennae (see, FIGS. 2 and 3 and the discussion infra) positioned at known locations relative to the instrument deck 18 (for example, at each one of a plurality of apertures 16 in the deck 18). The apertures 16 may be arranged in an array format or in some other useful configuration where each aperture has a known location. In a preferred implementation, there is one RFID tag reader antenna per aperture 16 (or known location) in the instrument deck 18, although the present teachings are not limited to such implementation. The RFID tag 12 can be oriented such that the RF coil 32 included within the RFID tag 12 is positioned near a bottom end 30 of the locating peg 10 (i.e., away from a body of the labware item), although such an example is merely indicative of one embodiment.

Figure 2:
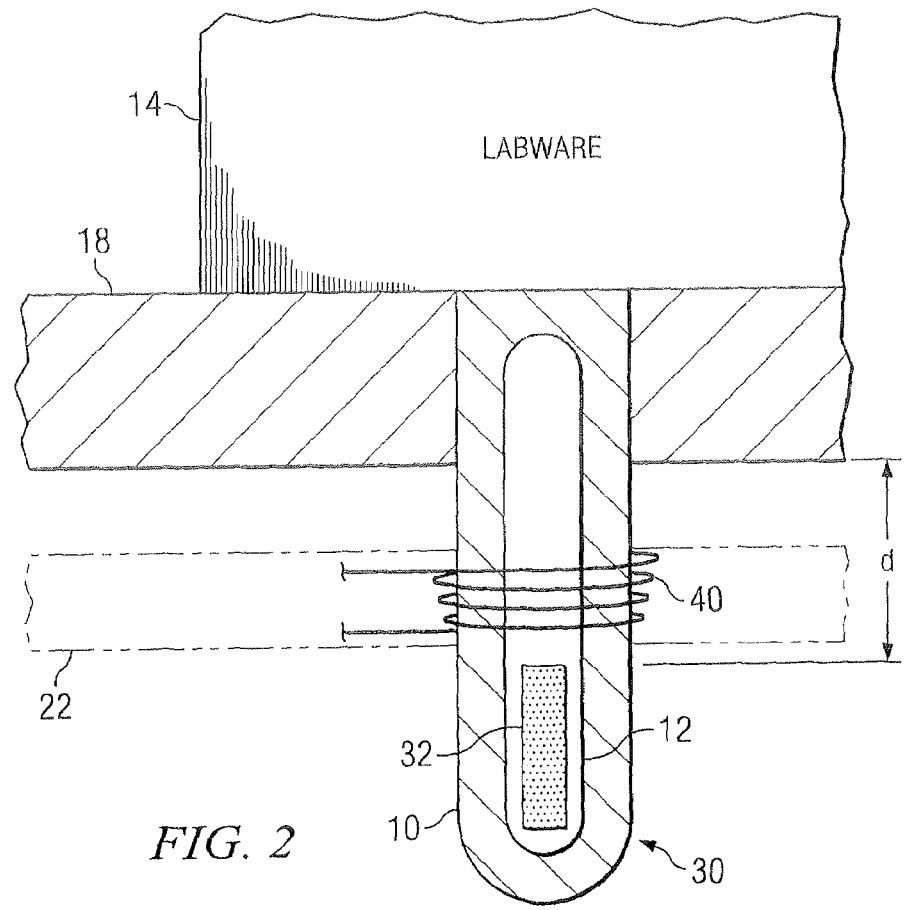
FIG. 2 includes a drawing of an RFID Tag.

FIG. 2 further illustrates an example of when labware may be positioned and/or mounted on the instrument deck, and the associated positioning of the RFID tag 12 (within the peg 10) relative to the instrument deck 18 and the PC board 22 reader antenna 40 (shown within a phantom PC board 22 outline). If the instrument deck 18 is fabricated from metal, the REID tag 12 can nonetheless communicate using an RF coil 32 provided that an/its RF coil 32 is positioned at least a distance "d" below a bottom surface of the metal deck 18, where such distance can vary based on the embodiment as provided herein. If the distance "d" is too small, the RF coil 32 within the tag 12 may have its signal shorted (or otherwise adversely affected due to interference, reflection, attenuation, etc.) by the metal deck. Accordingly, the distance "d" can be adjusted in the illustrated embodiments by adjusting the placement of the tag 12 within the peg 10 to avoid such a condition. For the illustrated embodiments, experimentation has shown viable, exemplary, distances d which would position an end of the RF coil 32 at a distance of between approximately 2 millimeters and approximately 8 millimeters from the reader antenna 40 on the surface of the PC board 22. In another implementation, the deck may be made of a non-metallic material which would allow for the RFID tag 12 (using its RF coil 32) to be in communication with the reader antenna 40 through the deck 18. This implementation may thus not require the use of pegs/apertures or alternatively would not require positioning of the RFID tag within the peg.

Figure 3:
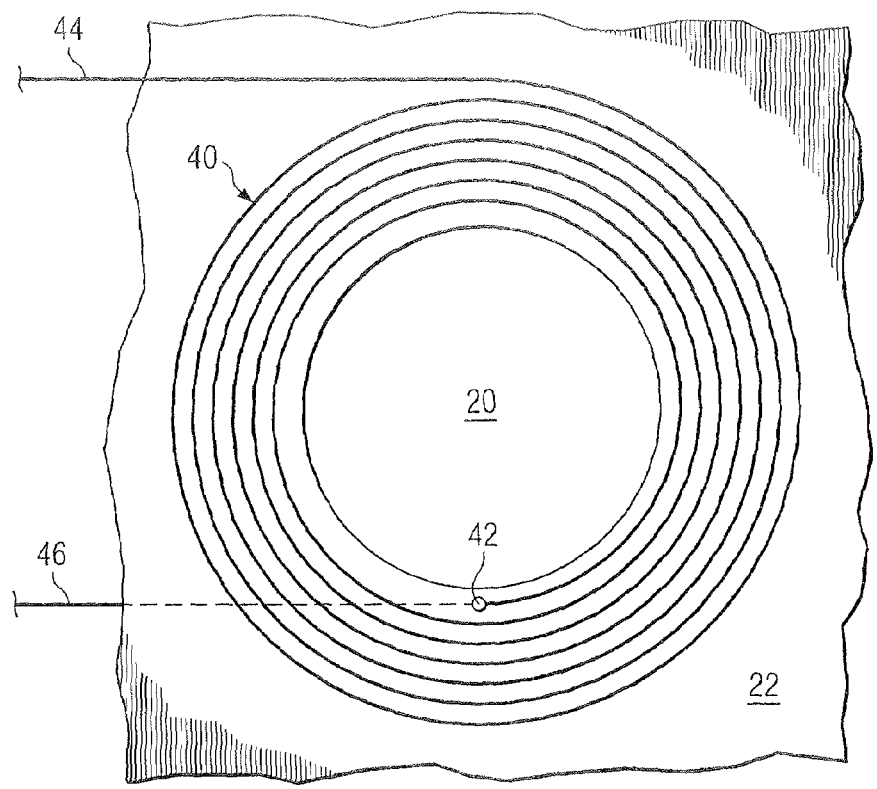
FIG. 3 depicts one embodiment of an RFID Antenna Coil.

The RFID tag reader antenna 40 and its associated circuitry can be designed and fabricated such that only tags 12 within a specified range of a particular reader antenna will be detected. More specifically, the antenna 40 may comprise a detection range antenna created by using a wire or PCB trace formed into a small (e.g., one-quarter to one-half inch) diameter spiral with a low number (e.g., 6-12) of turns. Although a circular spiral is shown in FIG. 3, it will be understood that other geometric spiral shapes (such as squares, rectangles, pentagons, hexagons, helixes, and the like) could alternatively be used. A short detection range for the antenna can be useful for reducing cross-talk among several closely spaced RFID tags such as would occur where a multitude of known locations on the instrument deck, each one having an associated antenna 40, are provided.

FIG. 3 shows just one exemplary embodiment of a short range RFID tag reader antenna coil. The coil for the antenna 40, along with one connecting lead or trace 44, can be formed on one surface of the PCB 22 surrounding the opening 20 in the PCB. A via 42 can then be formed at the other end of the antenna coil through the PCB 22 to a second side thereof for connection to a second connecting lead or trace 46 of the antenna 40.

Figure 4:
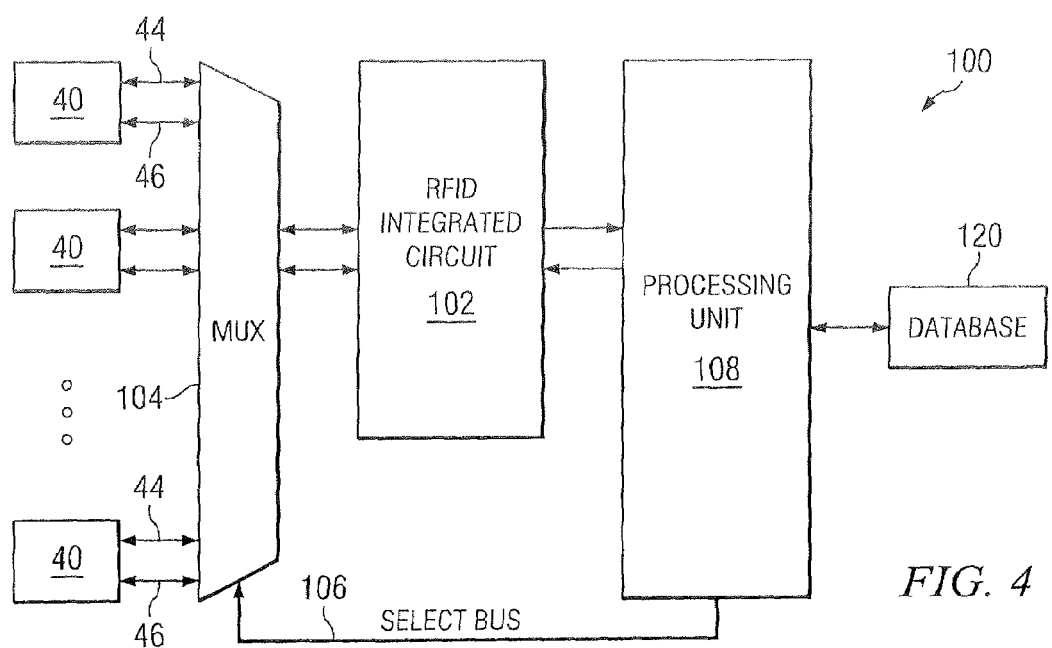
FIG. 4 represents a block diagram of an RFID Reader Circuit.

Reference is now made to FIG. 4 wherein there is shown a block diagram of an embodiment of a multi-RFID tag reader circuit 100. In one implementation, the circuit 100 utilizes an RFID tag reader integrated circuit IC 102 (e.g., Texas Instruments TMS3705A). The RFID tag reader integrated circuit IC 102 is selectively coupled by a multiplexer 104 to a plurality of antenna coils 40. These coils 40 are positioned associated with a corresponding plurality of known locations on the deck 18 (for example, at each of the apertures 16). Responsive to select signals supplied over a select bus 106, the multiplexer 104 chooses one of the coils 40 for connection with the RFID tag reader integrated circuit IC 102. The select signals are generated by a processing unit 108 which is also coupled to the RFID tag reader integrated circuit IC 102 to receive data output therefrom. The processing unit 108 could comprise a personal computer, a dedicated microprocessor, a microcontroller, or other suitable processing and control device.

In the illustrated embodiment, after an antenna 40 is selected by the processing unit 108 through the operation of the multiplexer 104, the RFID tag reader integrated circuit IC 102 first drives the antenna 40 with an AC waveform. This operation scans for proximately located RFID tags (i.e., tags near the location of the antenna 40) and serves to inductively charge a capacitor within each proximately located RFID tag 12 that is communicatively coupled to the selected and driven antenna(e) 40. In this regard it is to be noted that the RFID tag 12 can be a passive device which does not include its own battery power supply, but instead relies on the charged capacitor to provide power for RFID tag 12 operation. In such an embodiment, after the RFID tag 12 is charged, the RFID tag modulates its own RF coil 32 with its internal multi-digit numeric code (i.e., a unique identification code). The modulated RF signal is broadcast from the REID tag 12 coil 32 and received by proximately located antenna 40 (i.e., the antenna associated with the openings 16/20 through which the peg 10 and tag 12 extend). The RFID tag reader integrated circuit IC 102 which is coupled by multiplexer 104 to the receiving antenna 40 senses the broadcast signals coupled thereto and demodulates the signal to recover the transmitted numeric code. That recovered numeric code is then communicated by the RFID tag reader integrated circuit IC 102 to the processing unit 108 so as to identify the labware item. Because the processor also functions to select which antenna 40 is to perform a scan for proximate RFID tags, the processor can further determine location of the labware item on and/or near the deck 18. Still further, as will be discussed in more detail below, by noting the recovered numeric code and location information, the processor may further determine orientation of the labware item on the deck 18.

In one embodiment, one RFID tag reader antenna 40 can be placed beneath each labware locating hole 16 within the instrument deck 18, although as provided previously herein, it can be understood that in other embodiments, one RFID tag reader antenna 40 can be associated with multiple locating holes 16, and other variations can be made to the illustrated embodiment. As an example, locating holes 16 which receive labware pegs 10 can be spaced from each other on the instrument deck 18 by a distance of at least 20 millimeters or other suitable distance to reduce the risk of cross-talk or interference or mis-reads. In another embodiment, where locating pegs and locating holes are not required, one RFID tag reader antenna 40 can be placed beneath each known location on the surface of the instrument deck 18, or alternatively one RFID tag reader antenna 40 can be associated with multiple known locations on the surface of the instrument deck 18.

To save cost, several antennae 40 can be multiplexed (see, reference 104) into one RFID reader IC 102. The processing unit 108 can then be used to continuously select and "scan" or "poll" each antenna 40 (i.e., scan each locating hole 16 or known location), using the select signals on bus 106, so that the location and orientation of RFID-equipped labware 14 placed onto the instrument deck 18 can be detected as the labware is placed on or near the deck. For example, when the deck 18 is empty, the RFID tag reader IC 102 may scan/poll each antenna and return null values for each labware locating hole 16 (or known deck location), indicating that each locating hole 16 (or deck location) is empty (i.e., no labware present), where a "null" value is merely one example of a value representing the absence of labware. Continuing this example, when RFID tag 12 equipped labware 14 items are subsequently placed onto the deck 18, the RFID tag reader IC 102 may scan/poll each antenna and, with respect to the location where the labware is positioned (for example, at the locating hole receiving the locating peg), receives a communication from one or more RFID tags associated with that labware item. Thus, the reader could return non-null values for and/or corresponding to the locating holes 16 that contained labware pegs 10 (or with respect to certain known locations on the deck associated with the antenna(e) 40), thus indicating that labware 14 is present at those specific locations. Further continuing the example, it can be understood that removal of one or more labware 14 components from a deck 18 could cause a change, in a subsequent scan/poll of the antennae, from a non-null value(s) for respective locating holes 16, to a null value(s), thus indicating a removal event.

Once the data is read from an RFID tag 12, its pre-programmed numeric code (e.g., 64 bits or more) can be transmitted to a processing unit 108 and compared (in fill or in part) to numeric codes within a labware ID database 120. This database 120 accordingly may contain the RFID tag data codes of the tags embedded within each piece of labware. Based on the comparison, various events, actions, and/or decisions may be executed and/or enacted. For example, a match of part of the code can be used to determine the type of labware 14 present on the instrument deck 18. RFID tags 12 associated with (e.g., via communicative coupling) two locating pegs 10 on the same piece of labware 14 can allow a system to determine the position and orientation of the labware as well. For example, if the numeric code 11725550 is programmed into a first RFID tag and associated with (e.g., placed into) and/or communicatively coupled to the front, left corner locating peg 10, and the numeric code 11725551 can be programmed into a second RFID tag and placed into the rear, right corner locating peg 10, the "117" part of the code can be used to identify the type of labware present, the "2555" part of the code can be used to identify the specific labware item of type "117" (e.g., in case more than one "117" item type is present), and the last digit can be used to identify the location of one or more corners and/or other known and/or predetermined points of the labware, and hence the labware's location and/or orientation on the instrument deck 18. Such example is provided for illustration and not limitation.

It can be understood that one or more processors including but not limited to, for example, the aforementioned processing unit 108, may additionally and/or optionally be used in an event-driven manner to provide alarms and/or other event-driven communications to one or more other systems, sensors, etc. For example, removal of labware 14 may cause an alarm, while addition and/or depositing of labware at a certain location and/or orientation may cause a set of processor instructions to execute. Accordingly, event selection and/or management may be based on labware location, RFID tag, labware event (e.g., deposit, removal), labware type, and/or labware orientation, for example.

It can be understood that other variations of the present teachings include the elimination of locating pegs. For example, in embodiments where the instrument deck material does not present a communications issue (i.e., does not block radio frequencies), RFID tags may be otherwise coupled to labware using various techniques that do not include locating pegs, such that when labware approaches and/or is placed on the instrument deck, RFID tag readers/antennae placed at known locations on the deck may allow for communications with the RFID tags as otherwise provided herein. This would allow, just as with the foregoing discussion, for the identification of the labware type, as well as the identification of labware location and orientation on the deck 18.

Thus, disclosure is made of methods and systems for automatically locating and identifying labware using radio-frequency identification (RFID) tags. The methods and systems include a plurality of RFID tags (pre-programmed with unique data codes) embedded within the locating pegs of labware (or labware holders) or otherwise associated with labware (or labware holders). The methods and systems also include a plurality of RFID tag readers that mount near the locating holes of the deck of the instrument using the labware, or are associated with known locations on instrument deck. The RFID tag readers can scan (e.g., at programmed intervals, continuously, etc.) for the presence of RFID tags such that when a piece of labware is added to the deck, the readers can report to a processing device the specific location where (for example, locating hole in which) each tag was found, as well as the unique data code of each tag. By referencing a database that contains the RFID tag data codes of the tags associated with the various pieces of labware, the methods and systems can determine at least one of the location, orientation, and/or identity of the labware.

The methods and systems described herein are not limited to a particular hardware or software configuration, and may find applicability in many computing or processing environments. The methods and systems can be implemented in hardware or software, or a combination of hardware and software. The methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted.

As provided herein, the processor(s) and/or processing unit ("processor") can thus be embedded in one or more devices that can be operated independently or together in a networked environment, where the network can include, for example, a Local Area Network (LAN), wide area network (WAN), and/or can include an intranet and/or the internet and/or another network. The network(s) can be wired or wireless or a combination thereof and can use one or more communications protocols to facilitate communications between the different processors. The processors can be configured for distributed processing and can utilize, in some embodiments, a client-server model as needed. Accordingly, the methods and systems can utilize multiple processors and/or processor devices, and the processor instructions can be divided amongst such single or multiple processor/devices.

The device(s) or computer systems that integrate with the processor(s) can include, for example, a personal computer (s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," or processing unit, can be understood to include one or more processors that can communicate in a stand-alone and/or a distributed environment(s), and can thus can be configured to communicate via wired or wireless communications with other processors, where such one or more processor can be configured to operate on one or more processor-controlled devices that can be similar or different devices. Use of such "microprocessor" or "processor" terminology can thus also be understood to include a central processing unit, an arithmetic logic unit, an application-specific integrated circuit (IC), and/or a task engine, with such examples provided for illustration and not limitation.

Furthermore, references to memory, unless otherwise specified, can include one or more processor-readable and accessible memory elements and/or components that can be internal to the processor-controlled device, external to the processor-controlled device, and/or can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

References to a network, unless provided otherwise, can include one or more intranets and/or the internet, and can include wired and/or wireless networks. References herein to microprocessor instructions or microprocessor-executable instructions, in accordance with the above, can be understood to include programmable hardware.

Unless otherwise stated, use of the word "substantially" can be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun can be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, can be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, can be made by those skilled in the art. Accordingly, it will be understood that the methods and systems are not to be limited to the embodiments disclosed herein, can include practices otherwise than specifically described, and are to be interpreted as broadly as allowed under the law.

Although some embodiments of the disclosed method and apparatus have been illustrated in the accompanying Drawings and described in the foregoing Detailed Description, it will be understood that the disclosed methods and apparatus are not limited to the embodiments disclosed, but are capable of numerous rearrangements, modifications and substitutions without departing from the spirit of the disclosed methods and apparatus as set forth and defined by the following claims.

What is claimed is:

1. A system, comprising:
a plurality of labware items each having an RFID tag associated therewith;
an instrument deck having a top surface with a plurality of apertures for receiving a portion of a labware item, each aperture having at least one RFID reader associated therewith, the at least one RFID reader positioned at a known instrument deck location and configured to detect presence of a labware item in the aperture associated with the at least one RFID reader; and
wherein each of the plurality of labware items includes a bottom surface for engaging the top surface of the instrument deck, and each of the plurality of labware items includes a lower portion extending from the bottom surface and configured to extend into one of the apertures with the bottom surface in contact with the top surface of the instrument deck.

2. The system of claim 1 wherein the at least one RFID reader comprises an RFID reader antenna which is coupled to an RFID reading circuit.

3. The system of claim 2 further comprising:
a processing unit coupled to the RFID reading circuit and operable to cause the at least one RFID reader to scan for the presence of an RFID tag and determine from reading the RFID tag at least one of location, orientation, and identity of a labware item positioned on the instrument deck.

4. The system of claim 1 wherein the lower portion of each of the plurality of labware items includes at least one locating peg containing the RFID tag associated with the one of the plurality of labware items.

5. The system of claim 4 wherein each of the plurality of apertures is configured for receiving one locating peg.

6. The system of claim 5 further comprising a printed circuit board, mounted underneath the instrument deck, wherein the printed circuit board includes a plurality of openings, each of the plurality of openings aligned with one aperture in the instrument deck for receiving a locating peg.

7. The system of claim 6 wherein each RFID reader comprises an RFID reader antenna mounted to the printed circuit board and positioned adjacent an opening in the printed circuit board.

8. The system of claim 7 wherein the RFID reader antenna is a spiral antenna surrounding the opening in the printed circuit board.

9. The system of claim 6 wherein the printed circuit board is spaced away from an underside of the instrument deck.

10. The system of claim 5 further including a processing unit operable to cause the at least one RFID reader to scan for the presence of RFID tags and determine from reading at least one RFID tag that a labware item has been added to the instrument deck at a certain aperture.

11. The system of claim 1 wherein at least one RFID tag is programmed with a unique data code, and further comprising: a processing device operable to cause the at least one RFID reader to scan for the presence of RFID tags and determine from reading an RFID tag that a labware item having the unique data code has been added to the instrument deck.

12. The system of claim 11 further including a database coupled to the processing device and containing unique data codes for the RFID tags associated with labware items.

13. The system of claim 11 wherein the processing device further operates to determine location of the labware item added to the deck based on the known instrument deck location of the RFID reader and determine identity of that labware item based on the read unique data code.

14. The system of claim 11 wherein the processing device further operates to determine orientation of the labware item added to the deck based on the known instrument deck location of the RFID reader and the read unique data code of that labware item.

15. A method, comprising:
   associating an RFID tag with each of a plurality of labware items, each of the plurality of labware items having a bottom surface and each of the plurality of labware items having a lower portion extending from the bottom surface;
   providing a labware instrument deck including a plurality of RFID readers each positioned at a known instrument deck location, the labware instrument deck having a plurality of apertures, each associated with one of the RFID readers;
   placing the bottom surface of a first one of the plurality of labware items at a first location on a top surface of the instrument deck with the lower portion of the first one of the plurality of labware items extending into a first aperture; and
   reading an RFID tag associated with the first one of the plurality of labware items.

16. The method of claim 15 further comprising, based on reading the RFID tag, associating the read RFID tag with the first location.

17. The method of claim 15 wherein the lower portion of each of the plurality of labware items includes at least one locating peg and wherein associating comprises associating an RFID tag with each locating peg.

18. The method of claim 17 wherein placing includes inserting at least one locating peg in the first aperture.

19. The method of claim 15 further comprising, based on reading a plurality of RFID tags by plural RFID readers, detecting an orientation of a labware item.

20. The method of claim 15 wherein reading comprises:
   scanning for the presence of at least one RFID tag, and
   determining, based on a scanned RFID tags at least one of location, orientation, and identity of a labware item positioned on the instrument deck.

21. The method of claim 15 wherein at least one RFID tag is programmed with a unique data code and wherein reading comprises:
   determining that a labware item having the RFID tag with the unique data code has been added to the instrument deck at a particular instrument deck location.

22. The method of claim 21 further including storing in memory unique data codes for a plurality of RFID tags associated with labware items.

23. The method of claim 15 wherein at least one RFID tag is programmed with a unique data code and wherein reading comprises:
   scanning for the presence of the RFID tags programmed with the unique data code and reading the unique data code; and
   determining, based on the scanned RFID tag, location of a labware item and identity of that labware item from the read unique data code.

24. The method of claim 15 wherein at least one is programmed with a unique data code and wherein reading comprises:
   scanning for the presence of RFID tags and reading their unique data codes; and
   determining orientation of a labware item based on a read unique data code.

* * * * *